Figure 1:
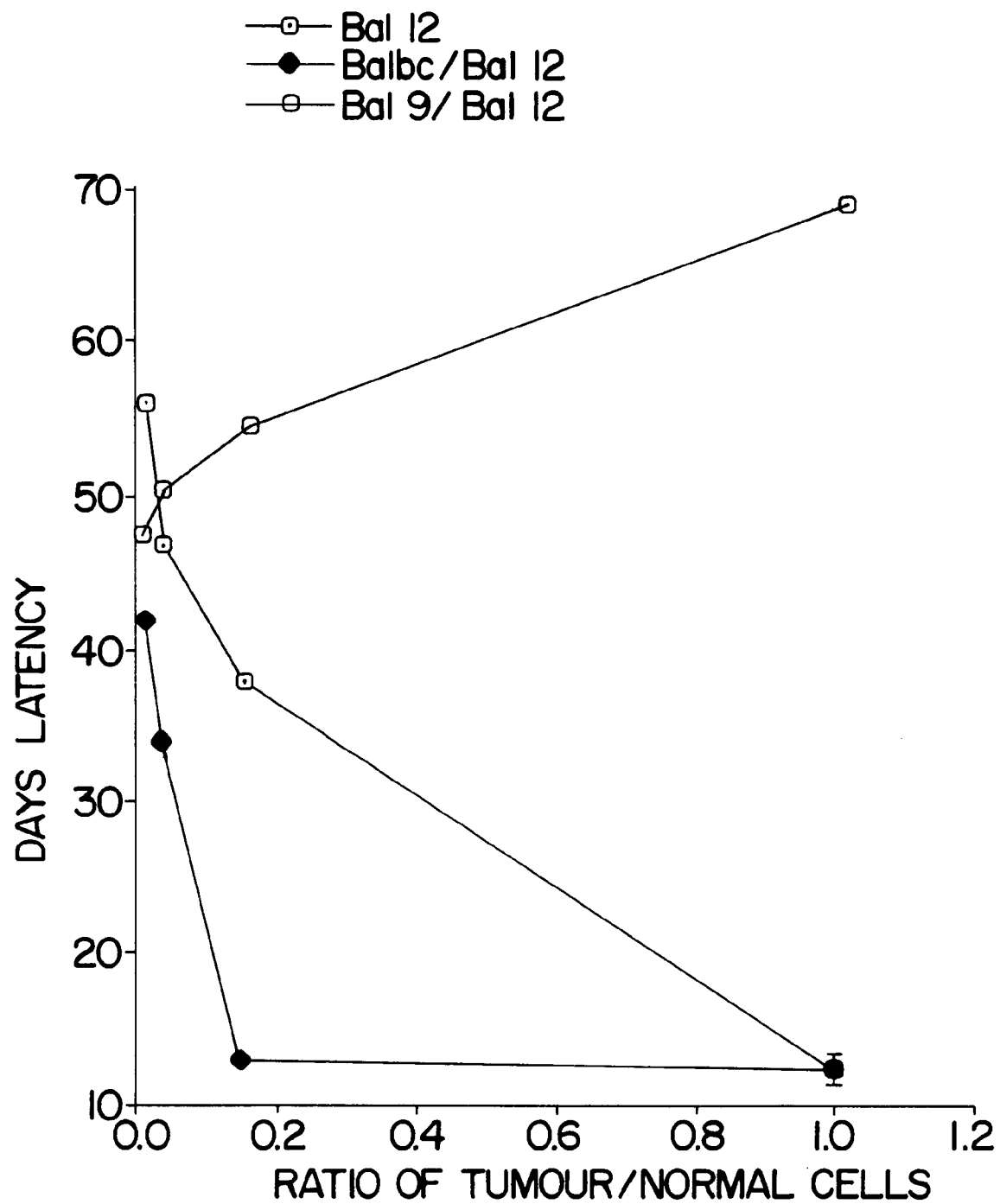

United States Patent [19]
Schofield et al.

[11] Patent Number: 5,902,788
[45] Date of Patent: *May 11, 1999

[54] INSULIN-LIKE GROWTH FACTOR II AS ANTITUMOUR AGENT

[75] Inventors: Paul Schofield, Cambridge; Robert Charles Rees, Sheffield; Amardip Singh Bhuller, Hertfordshire, all of United Kingdom; Anna Skottner-Lundin, Ekerö, Sweden

[73] Assignee: Pharmacia & Upjohn Aktiebolag, Stockholm, Sweden

[ * ] Notice: This patent issued on a continued prosecution application filed under 37 CFR 1.53(d), and is subject to the twenty year patent term provisions of 35 U.S.C. 154(a)(2).

[21] Appl. No.: 08/549,676

[22] PCT Filed: May 12, 1994

[86] PCT No.: PCT/GB94/01030

§ 371 Date: May 15, 1996

§ 102(e) Date: May 15, 1996

[87] PCT Pub. No.: WO94/26300

PCT Pub. Date: Nov. 24, 1994

[30] Foreign Application Priority Data

May 12, 1993 [GB] United Kingdom .................. 9310049

[51] Int. Cl.⁶ .................................................. A61K 38/30
[52] U.S. Cl. .................................... 514/3; 514/12; 514/2; 514/44
[58] Field of Search ...................... 514/2, 12, 44, 514/3

[56] References Cited

FOREIGN PATENT DOCUMENTS

89/05822  6/1989  WIPO .
92/19256  11/1992  WIPO .
93/00110  1/1993  WIPO .

OTHER PUBLICATIONS

Schofield et al., Tumour suppression associated with expression of human insulin–like growth factor II, Br. J. Cancer (1991), vol. 63, pp. 687–692.
Schofield, P.N. et al., *Cancer Letters*, 94: 71–77, 1995.
Zumkeller, W. et al., *J. Clin. Pathol.: Molec. Pathol*, 48:M333–M341, 1995.
Kohn, E.C. et al., *Int. J. Cancer*, 46: 287–92, 1990.
Granerus, M. et al., *J. Clin. Pathol.: Molec. Pathol.*, 48: M153–157, 1995.

*Primary Examiner*—Anthony C. Caputa
*Assistant Examiner*—Robert C. Hayes
*Attorney, Agent, or Firm*—Pollock, Vande Sande & Amernick

[57] ABSTRACT

The invention relates to the use of IGF-II for the manufacture of a medicament for the treatment of tumours, and especially for the manufacture of a medicament for growth inhibition of melanoma cells and for the treatment of cutaneous melanomas. The medicament can be systemically or locally administered.

3 Claims, 2 Drawing Sheets

INSULIN-LIKE GROWTH FACTOR II AS ANTITUMOUR AGENT

The present invention relates to the use of IGF-II for the manufacture of a medicament for the treatment of tumours and especially for the treatment of cutaneous melanomas.

The incidence of cutaneous melanomas in the United Kingdom is approximately 8000 per annum and is increasing; treatment of the disease is usually ineffective. Primary melanomas can be removed surgically and be subjected to biochemotherapy, but this is only marginally successful. Recent studies have shown that interleukin-2 based treatment regimes can result in an approximately 20 percent partial/complete response rate but there is a need to develop new therapies for treating disseminated tumours.

Melanomas of the ciliary body and choroid are the most common primary intraocular malignancy in adults and are fatal in approximately half of the patients. The incidence in the U.K. is seven per million per year. Death occurs within a 15 year period following initial treatment, and metastases, almost exclusively in the liver, are responsible for virtually all tumour related deaths. Median survival is less than six months. Despite the development of techniques which may preserve vision by obviating the need for enucleation or local removal, overall patient survival has remained unaltered. In most fatal cases, tumour dissemination has probably occurred before the patient presents for treatment. Recognition of early tumour spread, or identification of patients at most risk of developing metastases, coupled with, as yet, undefined forms of treatment aimed at the destruction of occult metastatic diseases remains our best hope for the future management of these tumours.

Insulin-like growth factor II (IGF-II) is a peptide present in plasma and other body fluids. It comprises 67 amino acids, including 3 disulphide bonds and its primary sequence shows 64% homology to IGF-1. It can stimulate growth of a wide range of cell types. IGF-II has been purified from human plasma and the complete amino acid sequence is known. Sequences with extensive homology to human IGF-II are present in IGF-II purified from plasma of other species. IGF-II has both systemic and local effects and appear to be mostly associated with different specific binding proteins, six of which are sequenced and are termed IGFBP1, IGFBP2, IGFBP3, IGFBP4, IGFBP5 and IGFBP6. These appear to modulate the biological functions and availability of IGF-II in both a positive and negative manner. IGF-II appears to act mainly by interactions with the IGF-type 1 receptor exposed on the outer surface of plasma membranes in many different cell types—however relative specificity of action may be found because of the influence of binding proteins. IGF-II may also have distinct actions as it binds to a distinct and unrelated type 2 receptor also found on cell membranes.

IGF-II has been shown to experimentally reduce the catabolic state in starved animals and to antagonise some metabolic actions of IGF-1 (Koea et al. Endocrinology 1992, 130, 2423–2425).

The insulin-like growth factors IGF-I and IGF-II have been shown to be mitogenic polypeptides with structural and functional homology to insulin. They are capable of supporting differentiation in many foetal and embryonic cell types, and for certain cancers the growth pattern may reflect IGF-I and IGF-II gene expression.

Heinze-Erian et al, Endocrinology, (1991) Vol 129, No 4, 1769, reports that there is an essential role for both IGF receptors in the regulation of cell mitogenesis and growth.

Commercial large scale production of IGF-II can nowadays readily be achieved by using recombinant DNA techniques.

A review is given by Schofield and Engstrom in The Insulin like growth factors Structure and biological functions, pages 240–57 (1992, OUP) regarding the expression of IGF-II by a wide range of human tumours.

The reason for the high degree of interest in IGF-II tumour expression is 1) because extrahepatic adult tissues do not normally make large quantities of IGF-II and
2) IGF-II is a mitogen for many cell types.

The logical conclusion is that IGF-II may act to produce unscheduled cell proliferation which may or may not initiate or promote tumour growth. However data differ from system to system, and although it is possible to demonstrate either potential or actual auto/paracrine growth from descriptive data, experimental data, dependent on either cell culture or xenograft culture, differ in their estimation of the potential rate limiting effect of IGF-II on tumour growth.

Schofield et al (Brit. J. Cancer, 63, 687–692 (1991)), in order to examine the potential role of IGF-II on tumour growth, constructed a recombinant retrovirus containing and expressing an IGF-II cDNA and used this to infect a cloned tumorigenic mouse fibroblast cell line. When the cells were infected into nude mice those clones expressing IGF-II from the DNA construct were found to initiate tumours with a much longer latency period than the parental, non-IGF expressing cell line. The interpretation of the published experiment is open to question. The experiment did not demonstrate that the antiproliferation effect seen was mediated directly by IGF-II and may have been due to another aspect of the construct, the cell line (for example interclonal variation in growth capacity) or the procedure devised to carry out the experiment.

Our studies have now shown that exogenous IGF-II, i.e. IGF-II given directly to the tumour under treatment, has an inhibitory or retarding effect on tumour growth but that IGF-I does not have this effect. This is unexpected and surprising and could not have been foreseen by earlier published results. IGF-II is traditionally held to be a mitogen rather than a cytostatic or cytocidal agent. Consequently this result is entirely counter-intuitive. There has been no prior report of an antiproliferative effect of IGF-II to date.

In order to demonstrate a direct effect of the peptide IGF-II on proliferation, direct delivery, with no intermediary process, was required. We report here the results of that experiment with supporting data, showing that, irrespective of a direct or indirect mechanism, the antiproliferative effect is consistent with an effect of the peptide itself.

The present invention relates to the use of IGF-II for the manufacture of a medicament for the treatment of tumours, especially for the treatment of cutaneous melanomas and for for growth inhibition of of melanoma cells. IGF-II is systemically or locally administered and could be given topically.

The invention also relates to a method for the treatment of tumours by administration of IGF-II.

FIG. 1: Effects of Co-inoculation of tumour latency

Figure 2:
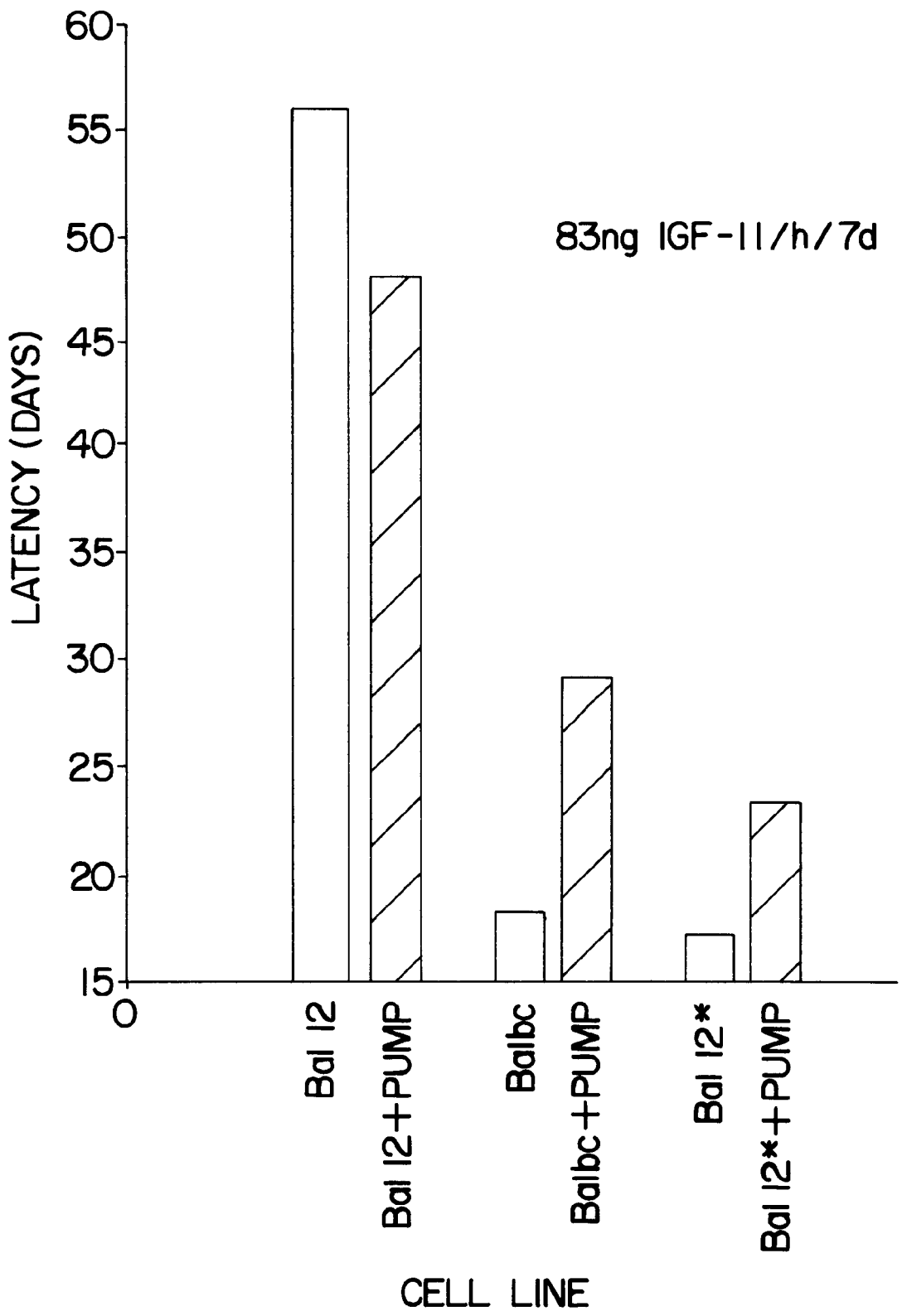

FIG. 2: Effects of exogenous IGF-II on tumour latency.

The used IGF-II has been produced by Kabi Pharmacia.

EXAMPLE 1

Growth inhibitory effects of IGF-II in vitro

In a series of experiments designed to evaluate the effect of IGF-II on a human melanoma cell line (A375) growth, it was noted in preliminary studies that IGF-II was growth-inhibitory.

a) IGF-II was added to three cell lines, namely human melanoma cell line A375 cells, a subline, NUPRI, derived by in-vivo passage of A375 and posterial uveal melanous cells, Mel 66. The cell lines were grown in microtitre plates in serum-free medium and DNA synthesis were assessed at 48 hours by pulsing the cells with $^3$H-thymidine. In an extensive series of experiments 10 ng/ml of IGF-II or greater concentrations were shown to inhibit cell proliferation as measured by $^3$H-thymidine uptake. See Table 1.

TABLE 1

Growth Factor effects on melanoma cell proliferation

| Growth Factor | Effect on cell growth of | | |
|---|---|---|---|
| | A375 | NUPR1 | Mel66 occular |
| IGF-I | No effect | Not done | No effect |
| IGF-II | Inhibition | Inhibition | Not done | b) The anti-proliferative effect of IGF-II was mediated either during late S-phase or in early G2/M as assessed by flow cytometry analysis. In these experiments IGF-II-treated A375 cells were stained with mithromycin and ethidium bromide and the proliferative phase of the cell cycle analysed.

The results are suggestive of a G2/M block in the cell cycle. In further studies using three other melanoma cell lines (a sub-clone of A375, NUPRI and Mel 66) it was shown that two of the three lines were also prone to growth inhibition by IGF-II. See Table 2 for the results with A375.

TABLE 2

| Growth Factor | Cells in $G_0/G_1$ | Cells in S Phase | Cells in $G_2/M$ |
|---|---|---|---|
| Control | 52.5 | 23.8 | 11.7 |
| IGF-II | 23.0 | 54.0 | 9.5 |

Control is the diluent without IGF-II

Our results shows that the growth of cutaneous melanoma cell lines is modulated by IGF-II, and that this effect possibly occures through the type 2 receptor binding site.

It is also shown that IGF-II and signal transduction following binding of this ligand to melanoma cells influences cell proliferation, and clearly this finding is of potential therapeutic significance.

EXAMPLE 2

Trans effect of expressing the peptide in mixed tumours.

Investigation whether suppression of tumour cell growth was mediated by a secreted signal, such as might be expected of IGF-II, or whether expression from the construct was affecting antonomous property of the cell.

This example confirms the earlier studies of Schofield et al and demonstrates that the effect of expressing IGF-II can be in trans (i.e. through a diffusible factor) and is subject to a dose response.

Tumorigenic and non tumorigenic construct containing cells in different ratios were mixed before injecting into nude mice. The number of tumorigenic cells was maintained at $5\times10^6$ per graft and suppessed cells added up to 20× this number. Control experiments demonstrated that whilst this did decrease tumour latency of the suppressed cells in an inoculum size dependant fashion the increase in untransfected cell latency was disproportionate.

A constant number of tumorigenic cells ($5\times10^6$) were inoculated into a single site along with an equal or greater number of suppressed cells at the ratios shown given in FIG. 1.

Balb/c means a parental tumorigenic clone cell
Bal12 means an IGF-II expressing cell
Balb/c/Bal 12 means a mixture of those cells.
Bal 9 means a cell expressing a low level if IGF-II
Bal 9/Bal 12 means a mixture of those cells
Bal 12 at differing inocula were used as control, i.e. the same number of cells as in the mixed grafts was put into each site alone.

In FIG. 1 is shown the number of days of latency when tumorigenic cells were inoculated together with normal cells at different ratios.

The data shown in FIG. 1 indicates that increasing numbers of suppressed IGF-II secreting cells are able to reduce the tumorigenicity of the parental cell line. This could either be due to metabolic inhibitory interactions unrelated to IGF synthesis or to a trans-acting property of the IGF-II construct bearing cells. Use of the low IGF-II expressing Bal 9 cell line indicated that the less tumorigenic grafts are more susceptible to the suppressive effects of being cografted with suppressed cells at a much lower input of suppressed cells, when compared to the parental balb/c line. This suggests that the trans effect is a consequence, direct or indirect, of IGF-II expression.

EXAMPLE 3

Effects of exogenous IGF-II on tumour latency $5\times10^6$ cells were transplanted to the usual suprascapular site mice and an Alzet osmotic minipump loaded with IGF-II dissolved in phosphate buffered saline/50 μg/ml BSA, Bovine Serum Albumin, (RIA grade) implanted nearby. In some instances a short catheter tube was attached to the end of the pump and attached via a single suture to the underlying muscle layer to stabilise it. In each case the orientation and proximity of the pump outlet to the graft was checked 12 hours later and on subsequent days, to ensure that displacement did not occur. After 7 days the pump was removed by making a small incision behind the rear of the implant and the tumour site monitored by palpation at 24 hour intervals. Tumour formation was scored as the first of two successive days on which a palpable lump could be felt beneath the skin. On resection this was usually found to comprise a distinct small tumour mass about 2–4 mm in diameter.

In FIG. 2, Bal 12* is a line of Bal 12 which spontaneously lost its IGF-II construct following continuous passage in culture in the absence of selective media. Latency is expressed in days between grafting and first palpation. Each data point is the average latency of tumours in 5 individual mice. The variation between latencies within a group was in every case within 10% of the mean.

$5\times10^6$ Balb/c parental cells were inoculated into 7 mice at day 0. Into two were placed osmotic minipumps (0.47 μl/hour loaded to deliver 21.5 ng IGF-II/hour) two received pumps delivering 42 ng/hour and a single mouse received a pump delivering 83 ng/hour. Mice were monitored by palpation daily and the time of first tumour palpation noted as before.

In FIG. 2 the effect of exogenous IGF-II on tumour latency is shown when a constant number of tumorigenic cells ($5\times10^6$) were inoculated into a single site along with an equal or greater number of suppressed cells at the ratios shown alone.

We have been able to demonstrate a dose dependency of latency of IGF-II delivered over 7 days. With a high correlation ($r^2=0.753$ and a correlation coefficient of 0.868) increased doses of IGF-II result in decreased tumorigenicity of the parental cell line.

We claim:

1. A method for inhibiting growth of cutaneous melanoma cells by administering an IGF-II polypeptide to a patient with cutaneous melanoma in an effective amount sufficient for inhibiting said growth.

2. The method of claim 1 wherein said IGF-II is systemically administered.

3. The method of claim 1 wherein said IGF-II is locally administered.

* * * * *